United States Patent [19]

Alvin

[11] Patent Number: 5,202,667
[45] Date of Patent: Apr. 13, 1993

[54] ELECTRIC LEAKAGE DETECTOR FOR UNDERGROUND STORAGE TANK SYSTEMS

[75] Inventor: David W. Alvin, Glen Ellyn, Ill.

[73] Assignee: Monitoring Systems, Inc., Oak Brook, Ill.

[21] Appl. No.: 600,538

[22] Filed: Oct. 19, 1990

[51] Int. Cl.$^5$ .................................................. G08B 21/00
[52] U.S. Cl. ...................................... 340/605; 73/49.2
[58] Field of Search ..................... 340/604, 605, 539; 73/49.2 T, 304 C; 361/284

[56] References Cited

U.S. PATENT DOCUMENTS

| | | | |
|---|---|---|---|
| 2,076,441 | 4/1937 | Berry | 340/604 |
| 3,771,548 | 11/1973 | Rauchwerger | 340/605 |
| 3,824,460 | 7/1974 | Gustafson | 361/284 |
| 3,986,110 | 10/1976 | Overall | 340/605 |
| 4,206,402 | 6/1980 | Ishido | 73/40.5 R |
| 4,319,232 | 3/1982 | Wetphal et al. | 340/604 |
| 4,468,609 | 8/1984 | Schmitz | 340/605 |
| 4,586,033 | 4/1986 | Andrejasich | 340/605 |
| 4,591,946 | 5/1986 | Pope | 361/284 |
| 4,601,201 | 7/1986 | Oota et al. | 361/284 |
| 4,638,920 | 1/1987 | Goodhues, Jr. | 73/49.2 T |
| 4,644,354 | 2/1987 | Kidd | 73/49.2 |
| 4,660,026 | 4/1987 | Chandler | 340/605 |
| 4,710,550 | 12/1987 | Kranbuehl | 526/60 |
| 4,740,777 | 4/1988 | Slocum et al. | 73/49.2 T |
| 4,818,976 | 4/1989 | Schmitt et al. | 340/605 |
| 4,973,946 | 11/1990 | Cowden, II | 340/605 |

Primary Examiner—Edward L. Coles, Sr.
Assistant Examiner—Jill Jackson
Attorney, Agent, or Firm—Charles C. Valauskas

[57] ABSTRACT

A fluid detection system by which the presence or absence and identity of fluids may be detected within confined areas, such as those existing within underground storage tank systems and in which fluids may accumulate. The fluid detection system includes a probe assembly having circuitry which determines the presence of fluids by the capacitance developed across a variable capacitor. The output signal provided by the capacitor is converted to frequency values, is filtered by a receiver included with the system, and transmitted to a remote location for display. The system is suitable for deployment within and monitoring of one or a multiple of tank systems.

29 Claims, 12 Drawing Sheets

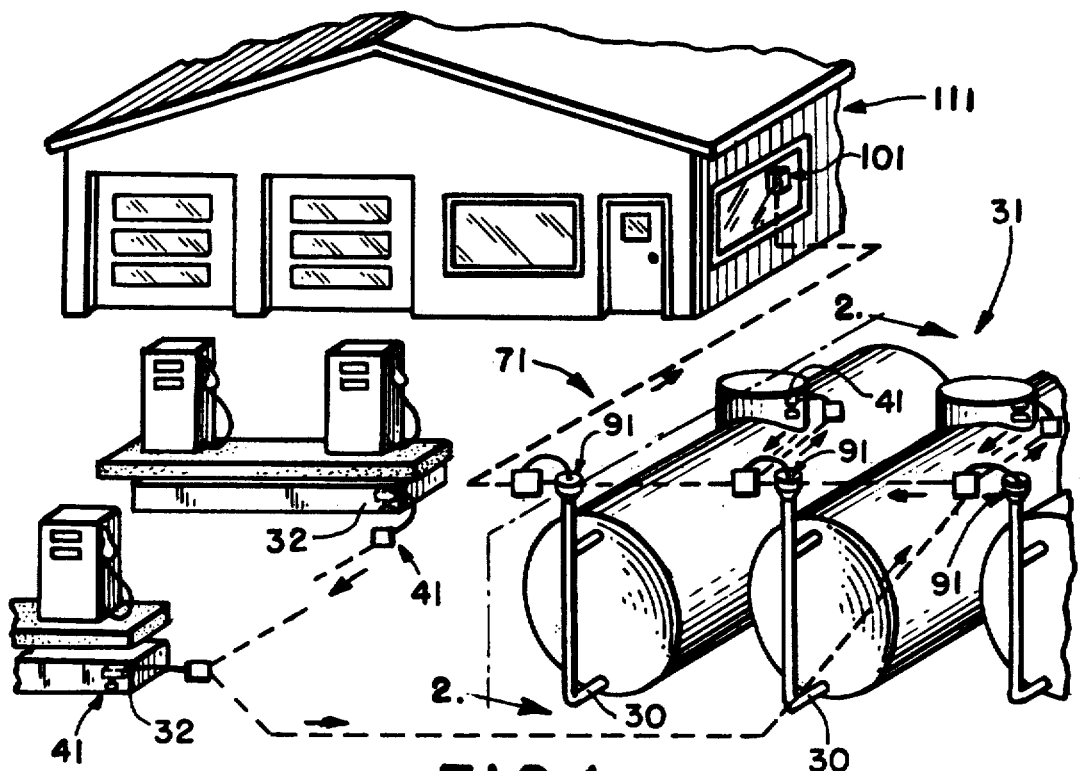
FIG. 1
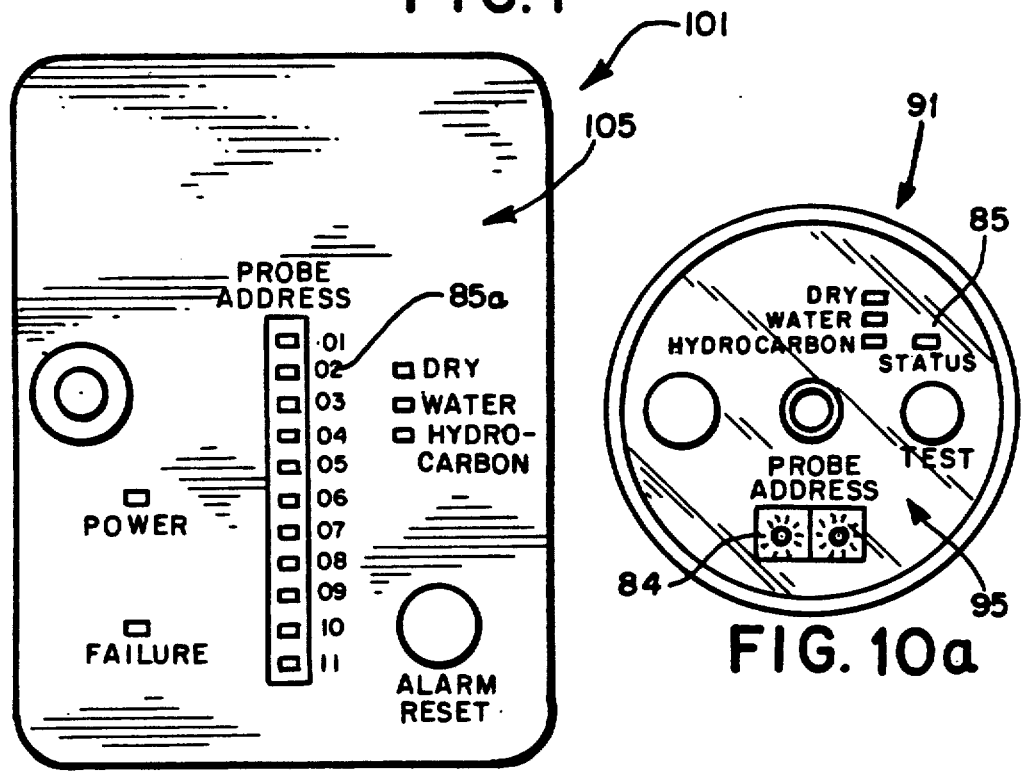
FIG. 10a
FIG. 10b

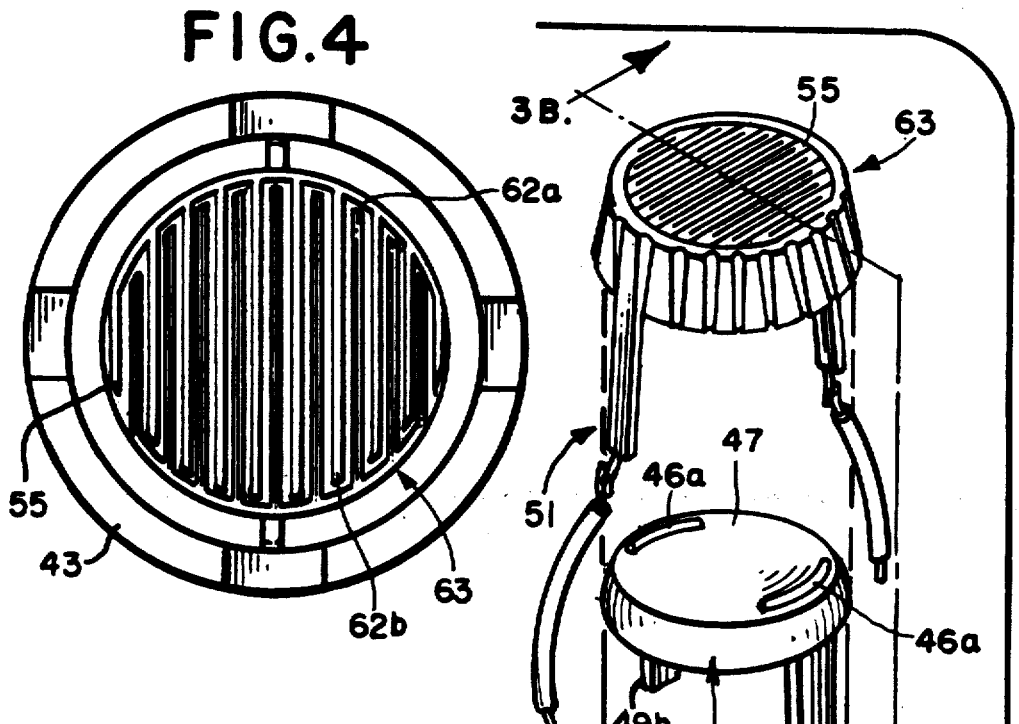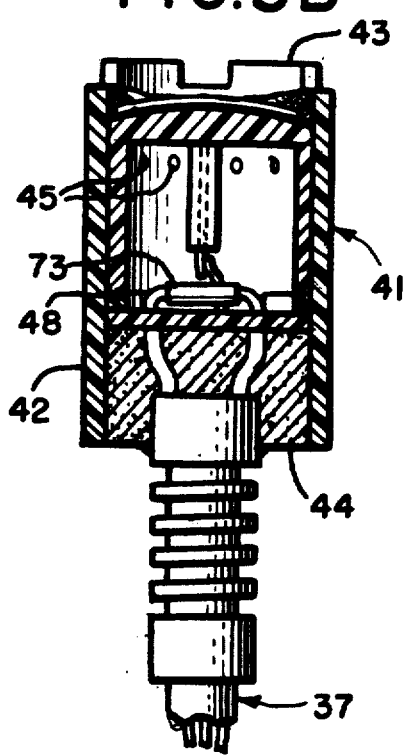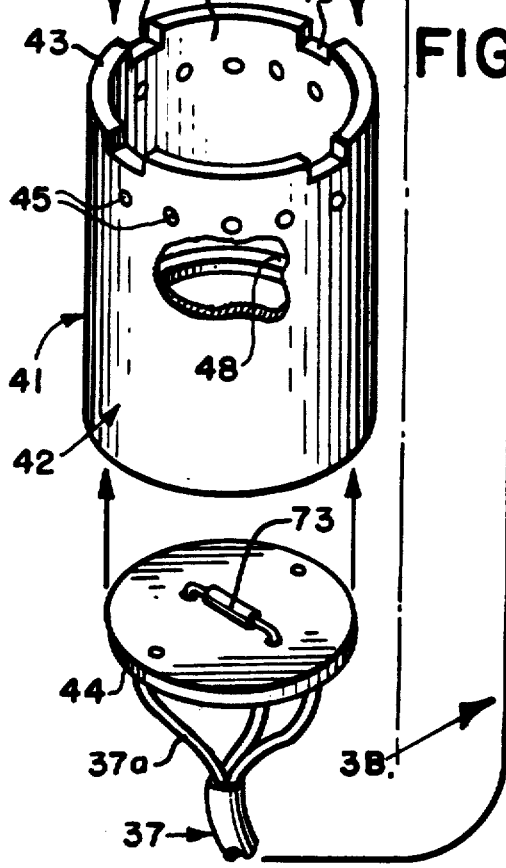

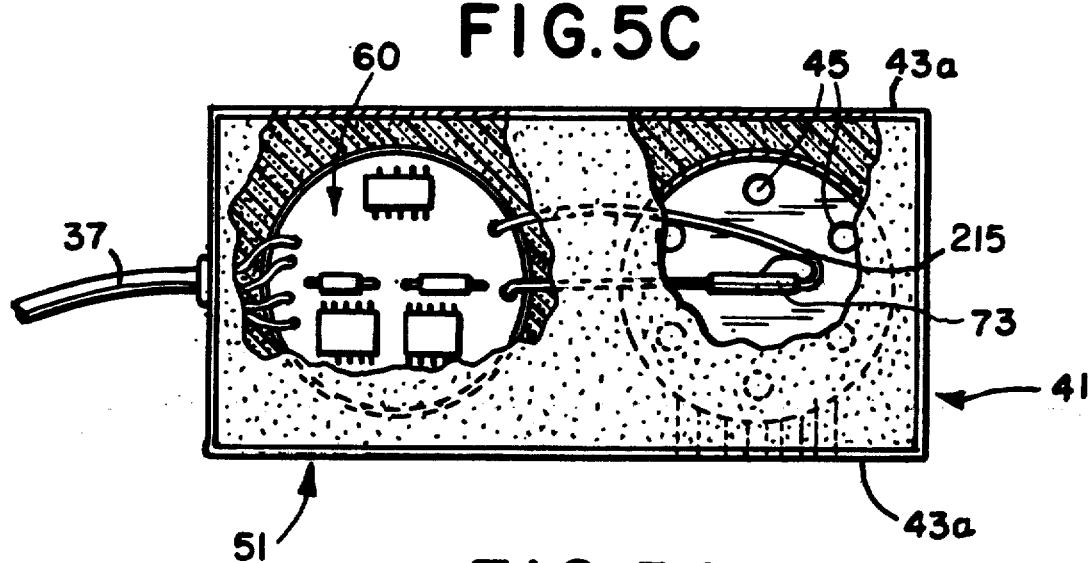
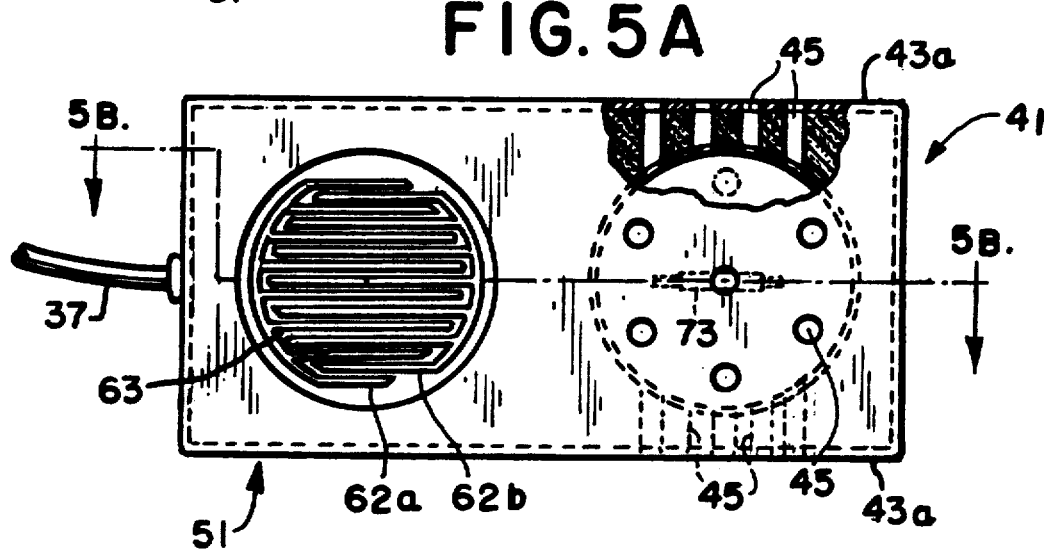
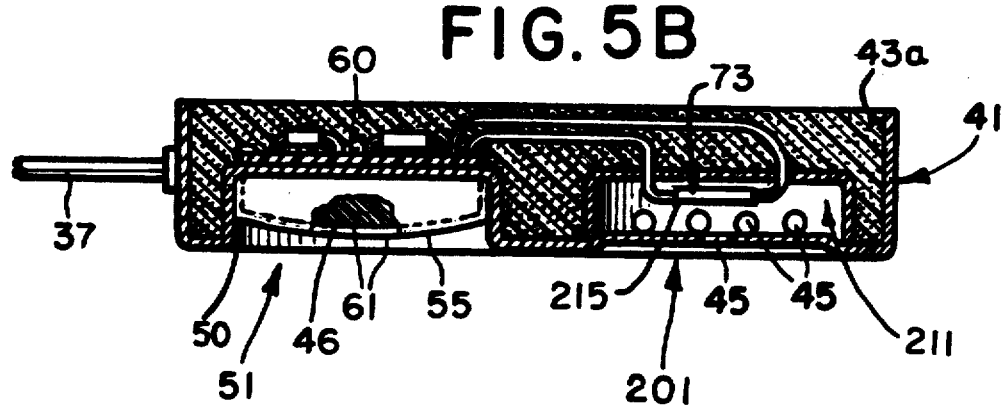

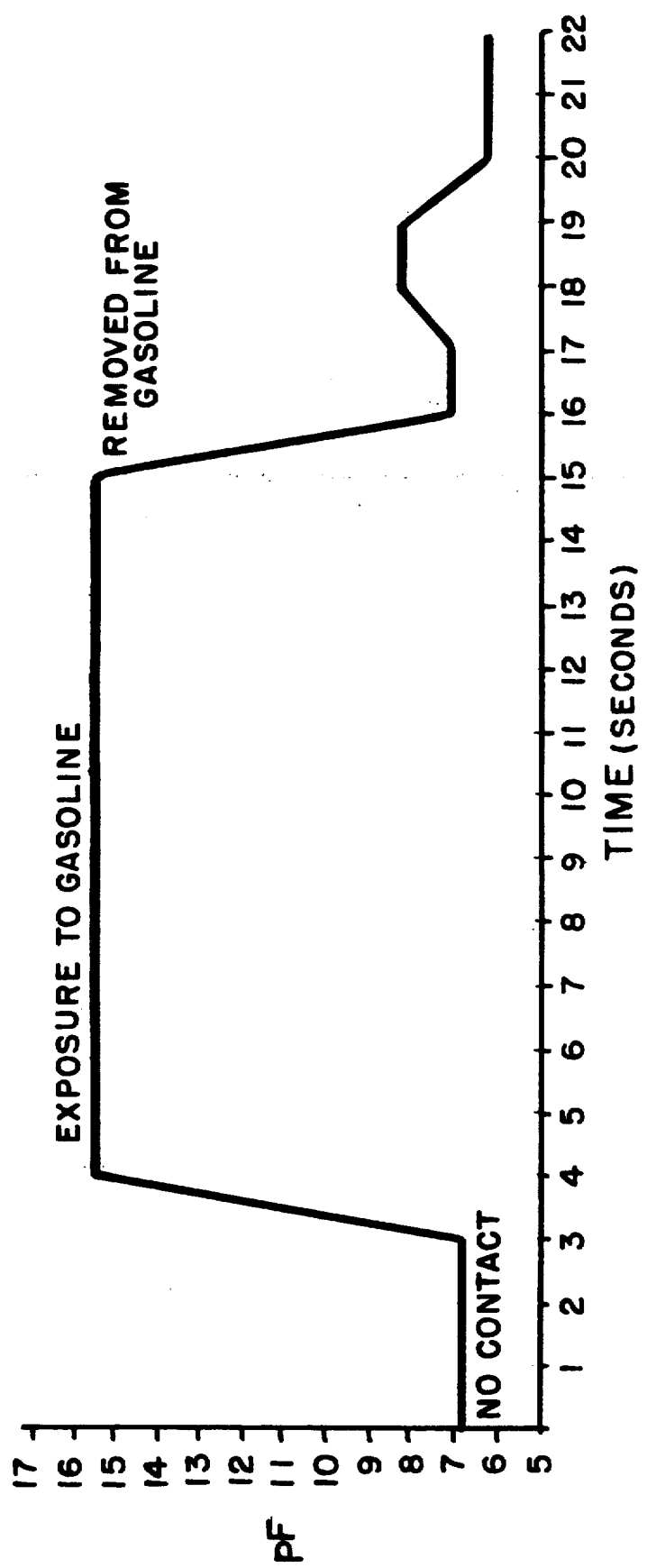

ELECTRIC LEAKAGE DETECTOR FOR UNDERGROUND STORAGE TANK SYSTEMS

BACKGROUND AND DESCRIPTION OF THE INVENTION

The present invention generally relates to a detection system. More particularly, the invention relates to a detection system by which the presence or absence and type of fluid unintentionally or accidentally present in confined areas, such as within an underground storage tank system may be identified.

In certain systems, the presence of fluids is unwanted and may be indicative of a more serious problem. Underground storage tank systems include confined areas in which the presence of fluid may be indicative of a serious problem.

An underground storage tank is any tank that has at least a portion of its volume positioned below ground level. The tanks are largely made from metal, such as steel with or without coating, or synthetic materials, such as plastic or fiberglass. One type of underground storage tank, the double-walled underground storage tank, is constructed such that an inner wall retains the stored fluid or substance and a surrounding, but separate, outer wall acts to confine any fluid that leaks from the inner wall and to maintain the integrity of the inner wall. It is into the interstitial space that opens between these walls that ground water from the outside may enter or that leaked fluid from the inner wall may enter, such as after a portion of the wall has corroded away or has been disrupted by the shifting of the underlying or surrounding soil or by unsupervised digging.

An underground storage tank is one part of a system that includes piping by which the fluid or substance to be stored in the tank is delivered to the tank and by which the same fluid or substance is drawn from the tank, such as with the use of a dispenser. Any one location may have a plurality of such tank systems. An example of such a location having a plurality of tank systems is a gasoline service station in which products, such as different grades of gasoline may be stored in and dispensed from different underground storage tanks. Dispensers at such a location consist of conventional gasoline pumps. In order to protect the tank system piping from disruptive effects, and to prevent spills— that occur during the filling of or dispensing from the tanks—and leakage from the piping from entering the surrounding environment, underground tank storage systems may include one or more containment chambers. Such chambers generally surround, for example, the area at which products are delivered to the tank and the areas from which the products are dispensed from the tank.

Underground storage tanks, particularly those that are buried completely below ground, are the preferred means to store and dispense fluids—such as gasoline, oils, petroleum products, chemicals—that are toxic and/or hazardous. Underground storage tanks are proportionately less exposed and thereby better protected from accidental rupture. Furthermore, if such tanks do leak or spills do occur, the fluid is accepted into the surrounding soil thereby preventing immediate exposure to the public. Furthermore, placing the tank underground saves above ground space for other purposes.

Given the need for and advantages of underground storage tank systems, it is not surprising that there are an estimated several million such systems currently in use throughout the United States. One of the largest uses of underground storage tanks is for the storage of gasoline and related fuel products at services stations across the country.

One serious consequence that occasionally results from the use of underground storage tanks, however is the emission of product when it is being delivered to, stored within, and/or drawn from the tank. The product as stored within the tank may be leaked into the environment because of corrosion, disruption, and/or faulty installation of the tank, the system piping, and/or the dispenser. Underscoring the leakage problem is that it is estimated that some twenty-five percent of all underground storage tanks are said to be now leaking.

Substances leaking from tanks can contaminate the surrounding soil, air, and ground water. Contamination of the ground water supply is serious since some fifty percent of the U.S. population still depends on ground water as a source of drinking water and because ground water is a resource that is renewed at a particularly slow rate. Depending upon the type of fluid or substance that is leaked, poisonous and/or explosive vapors may result. These vapors tend to accumulate in confined spaces such as basements, septic tanks, or sewers causing hazardous and possibly life threatening situations. Tank leaks are costly not only because of the loss of the stored product and because of the fines that may be imposed under federal, state, and/or local laws, but also because ultimately the released product must be cleaned up. Clean-ups often cost $100,000. or more.

A variety of devices and methods by which leaks from underground storage tanks may be detected are known. However, a variety of disadvantages are associated with them. For example, double-wall underground storage tanks made of a metal or coated metal conventionally include a monitoring pipe extending vertically adjacent to and generally approximate to one or more of the corners of the outer wall of the tank. A section of pipe opens between the monitoring pipe and the tank such that any fluid that leaks onto the inner basal area of the interstitial space—either because of a breach of the outside wall or a breach of the inner wall of the tank—may drain toward and onto the floor of the monitoring pipe. Whether a leak has occurred from a tank containing gasoline or other volatile fluid is determinable from the vapors that will be emitted. The vapors are detectable upon removal of the surface cap of the monitoring pipe. The presence of non-volatile fluids in the monitoring pipe, such as water, is conventionally detected by lowering and retrieving a sampling device down the length of the monitoring pipe. Such a sampling device may be as simple as a long cloth rag. Similar known methods and devices are used to detect the presence of leaked or spilled fluids in containment chambers. One of the many problems associated with such monitoring devices and methods is that they require personal attention and do not provide continuous monitoring. Without continuous monitoring, a leak may go undetected for a long period of time thereby allowing what may be a minor problem to become exacerbated.

Other conventional systems signal the presence of fluid in the detection area by the movement, for example, of a probe. Such a probe system may include a float that signals that a leak has occurred upon the float being buoyed up by the liquid.

Systems that utilize moving parts, such as floats, are particularly problematic in that they do not identify the presence of a leak until a sufficient amount of liquid has collected so the float can be buoyed up. If the fluid does not collect in such a way as to buoy up the float, the signal is not triggered. Furthermore, the float's ability to become buoyant depends not only on the material characteristics of the float and its own weight, but also the weight of that which is attached to the float. Very often power lines and/or guide wires are attached to the float. These elements act to weigh the float down. Floats can also bind, get caught, hang up, or lose their buoyancy with time, thereby decreasing the ability of the system to identify that a leak is occurring.

Other conventional systems utilize certain means to detect the presence of a fluid chemically or electrically. These known probes are disadvantageous in that they have a generally limited period of usefulness and/or cannot be reused. For example, some such probes utilize exposed metal surfaces to sense the presence of a fluid. However, the effectiveness of such probes largely decreases with time and exposure because the metal surface oxidizes and/or becomes covered with film or dirt. Other probes utilize a reactive face that changes in response to a liquid such as by undergoing an irreversible chemical reaction. Such probes must be replaced after contact with a liquid is made.

Many known detection systems are limited in their applications. For example, some systems can be positioned in the interstitial area between the walls of a double walled tank system, or in a monitoring pipe, or in a containment chamber around piping or under a dispenser, but not necessarily in all of these applications. Other systems are capable of detecting one or a very limited number of fluids but are generally not tunable to selectively detect one or more of a wide range of fluids.

Other known systems that do utilize some type of circuitry to identify leaks tie the electrically-powered probe to a control assembly by conventional means, such as lengths of wire. Such systems are generally not reliable because the noise that may be generated over a length of the wire is not filtered out thereby giving rise to spurious signals.

A demand therefore exists for a system and methods with which the presence or absence of fluid within, for example, the interstitial space between the inner wall and outer wall of an underground storage tank, within the monitoring pipe adjacent to an underground storage tank, and/or within a containment chamber—such as which surrounds the piping leading to or from an underground storage tank or that is below and surrounds the piping to a dispenser—may be monitored reliably and on a continuous, unattended basis. The present invention satisfies this demand.

The fluid detection system of the present invention uses the capacitance that develops across an unique comb-like electrode assembly within a unique liquid sensing probe to identify the presence and/or absence of a fluid and, more specifically, the type of the fluid that may enter a confined area within an underground storage tank system. It is known that the capacitance between two closely spaced, but separate, plates will also be affected by the distance between the plates: the greater the distance between the plates, the lower the capacitance developed across the circuit. Capacitance will be affected also by the material—termed the dielectric—present between the plates. Each dielectric is assigned a dielectric constant that is indicative of the ability of the dielectric to affect the capacitance generated across a circuit. Air has a dielectric constant of one. The system of the present invention utilizes the particular dielectric constant, or signature, that each fluid has to identify the presence or absence of and the type of fluid that is encountered by the electrode assembly in the system.

More particularly, a detection system according to the present invention includes a assembly designed to monitor conditions within and to detect the presence and/or absence and types of fluids in confined areas in which inspection, visually or otherwise, is generally impossible or difficult to accomplish on a regular and/or cost effective basis. Such confined areas include those areas within underground storage tank systems where fluids unintentionally or accidentally entering the system can accumulate, such as the floor of a monitoring pipe, the floor of a containment chamber, or the inner basal area of the interstitial space between the walls of a double-walled tank. The probe includes a sensor that is positionable approximate to, but separate from an accumulation area. Within the probe, a sensor having specialized solid state liquid sensing circuitry and, in particular, a electrode assembly across which, in response to contact with a fluid or substance present in an accumulation area, capacitance develops that is characteristic of the fluid or substance. The system circuitry responds to the capacitance of the electrode assembly by generating a variable frequency signal for transmission to a surface-mounted, analyzer unit. The liquid sensing circuitry further includes within the analyzer unit, logic by which frequencies characteristic of humidity and/or temperature ambient conditions, and frequencies characteristics of fluids not of interest, are removed from the output signal. The edited output signal is digitized and transmitted to a central display location, located for example, above ground and remote from the underground storage tank system.

The detection system of the present invention may be advantageously used in a variety of applications. For example, the probe assembly may be lowered into the interstitial space between the walls of a double-walled underground storage tank, lowered into monitoring pipes, such as those typically associated with metal or metal underground storage tanks, or positioned within the containment chambers that are approximate to the filling area and/or dispensing area of such tanks.

The detection system utilizes no moving parts, such as a float, that can hang up or otherwise provide a false reading. Instead, the probe assembly is capable of identifying the presence or absence of fluids by a specialized sensor circuitry. The detection system does not require a great amount of fluid to accumulate before the presence of the fluid is identified. A liquid film accumulation as shallow as one thirty-second of an inch may be identified by the detection system.

The sensor of the present invention has no elements that are exposed or otherwise can be altered, especially in the presence of the fluids to be monitored. The probe assembly detects without the destruction of the sensor thereby obviating the need to replace the sensor after a single contact with fluid.

The sensor circuitry of the probe assembly furthermore may be tuned to the capacitance generated by water and any one of a variety of fluids, including gasoline, petroleum, diesel fuel, or methanol.

The sensor is advantageously positionable by the probe assembly approximate to but separate from the accumulation area to prevent the system from providing the false readings that intimate contact with the accumulation area would provide.

The probe assembly of the present invention provides a variable frequency output signal. A signal provided in this form is less subject to interference by customary occurrences, such as adjacent power lines or variations in power line voltage.

The variable frequency output signal generated by the probe assembly of the system is analyzed by an "intelligent" frequency counter which reads the signal on a constant basis and separates frequencies, such as that generated by "noise", fluids of no interest, and that generated in response to ambient moisture and temperature conditions.

The resulting output signal is digitized to allow the signal to be reliably transmitted over long distances without risk of electrical interference. The signal may be displayed at a location, such as a ground level display, and/or at a remote location such that the conditions within a multiple of accumulation areas may be displayed at once.

It is, accordingly, a general object of the present invention to provide a system by which conditions within underground storage tank systems may be monitored.

Another object of the present invention is to provide a system that is capable of detecting the presence and/or absence of a wide range of fluids, including water.

It is an additional object of the present invention to provide a detection system by which one of a variety of fluids may be separately identified within an accumulation area of an underground storage tank system.

It is a further object of the present invention to provide a system that includes a sensor that contains no exposed metal surface or reactive surface and that is not prone to oxidation and/or corrosion or otherwise is alterable in response to the presence of a fluid.

A further object of the present invention is to provide a system that includes a sensor by which the presence or absence of and identity of a wide range of fluids may be detected reliably and continuously.

Also an object of the present invention to provide a system that includes a sensor that can detect a wide range of fluids without the destruction of and need for the replacement of the sensor.

Another object of the present invention is to provide a system that includes circuitry by which signal noise, such that generated by ambient conditions and nonselected fluids may be filtered out.

Additionally, an object of the present invention is to provide a system that includes a transmitter by which the signal may be digitized for transmission without a loss in information.

These and other objects, features, and advantages of this invention will be clearly understood and explained with reference to the accompanying drawings and through a consideration of the following detailed description of the preferred embodiments.

BRIEF DESCRIPTION OF THE DRAWINGS

FIG. 1 is a diagrammatic view of embodiments of the instant invention in an operative environment and as positioned within an underground storage tank system;

FIG. 3A is an exploded perspective view of one embodiment of the probe assembly of the present invention;

FIG. 3B is a side view of the probe assembly illustrated in FIG. 3A partially sectioned;

FIG. 4 is a front detail of the sensor showing the flat variable capacitor as positioned in the probe assembly illustrated in FIGS. 3A and 3B;

FIG. 5A is a front view of another embodiment of a probe assembly according to the present invention;

FIG. 5B is a side sectional view of the embodiment illustrated in FIG. 5A;

FIG. 5C is a back view of the embodiment illustrated in FIGS. 5A and 5B partially cut away to illustrate the probe assembly circuit board and vapor sensing assembly;

FIG. 9B illustrates the effect that exposure of the present invention to air and to gasoline fluid has on capacitance developed across the capacitor circuitry;

FIG. 10A illustrates the display panel of a cap of a probe assembly according to the present invention; and FIG. 10B illustrates the display panel of a monitor console unit of the present invention.

DESCRIPTION OF THE PARTICULAR EMBODIMENTS

Figure 2:
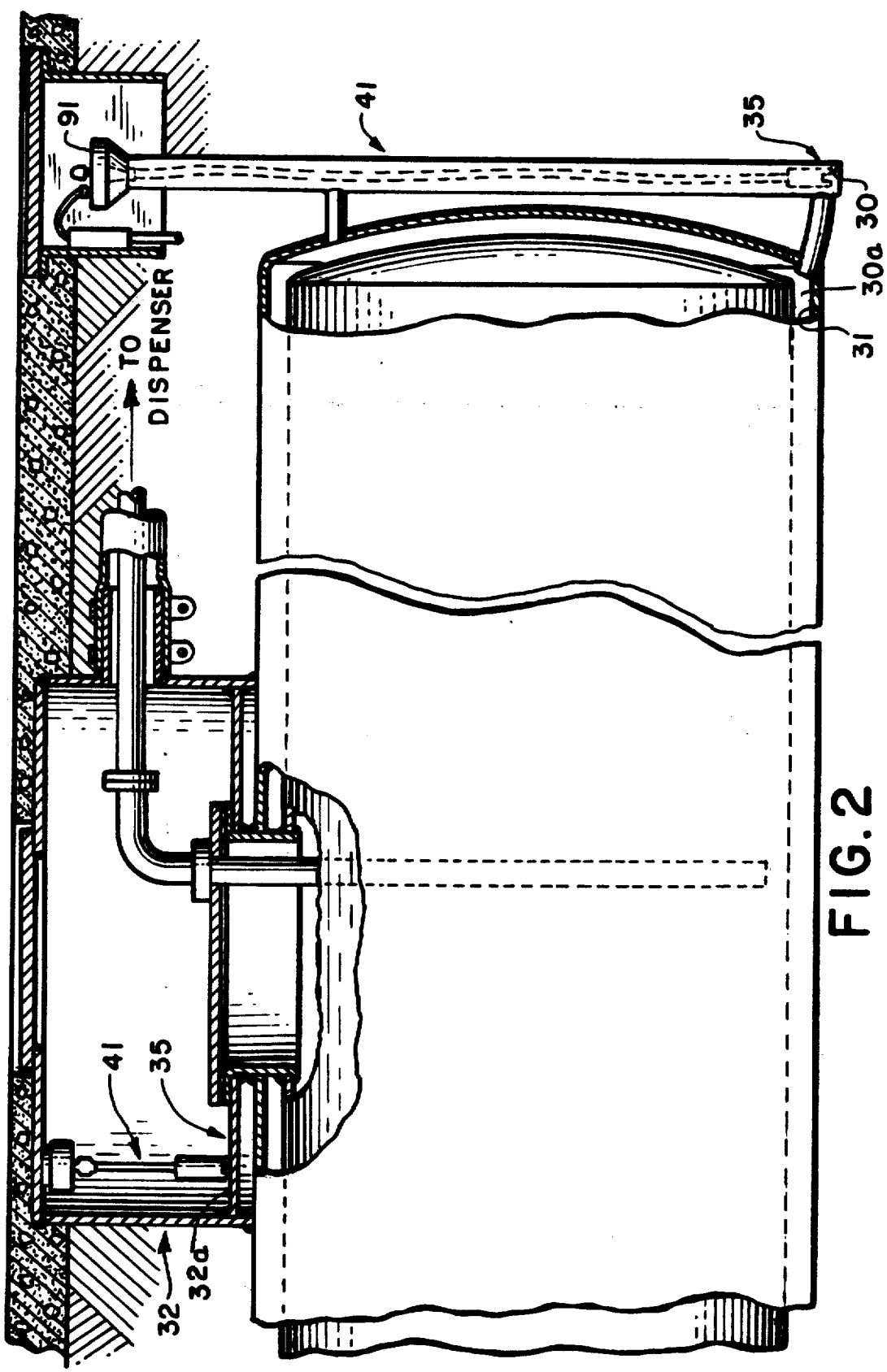
FIG. 2 is a sectional view of one embodiment of the instant invention as positioned within the monitoring pipe and containment chamber of an underground storage tank.

A fluid detection system according to the instant invention is designated in FIGS. 1 through 8 and 10 as 31.

Fluid detection system 31 includes a probe assembly 41 positionable within a confined area in which inspection, visually or otherwise, is generally impossible or difficult to accomplish on a regular and/or cost effective basis and where fluids may accumulate. Accumulation areas 35 within a confined area of an underground storage tank system include the floor of a monitoring pipe, the inner basal area of the interstitial space of a double-walled tank, and the floor of a containment chamber.

Probe assembly 41 includes a sensor 51 having associated circuitry 60 that preferably operates using a low-voltage, low-amperage power source. The ability of the circuitry 60 to operate using such a power source is mandatory for reasons of safety particularly when the system 31 may be used in the presence of and/or to detect explosive and/or flammable fluids.

Power may be supplied through a lead 37a included on and the probe assembly 41 is generally positionable on an accumulation area 35 by connection means in the form of a cable 37. Cable 37 is made of a material having sufficient compliant strength so that, for example, the probe assembly 41 may be lowered down a monitoring pipe. In addition to a power lead 37a, cable 37 may include a ground lead 37b, and a data lead 37c by which data generated by the sensor 51 may be transmitted for display.

Fluid sensing capacitor 63 is structured to distinguish between different fluids and substances by changes in the capacitance developed across the capacitor upon contact with the fluid or substance. The capacitor 63 is constructed of wire traces 62a, 62b made from a material across which charge may be readily developed and held. Such material includes copper, palladium, or platinum. The wire traces 62a, 62b are preferably arranged so that the amount of surface area available for contacting a sheet of liquid or substance is maximized. Wire traces 62a, 62b arranged flat in interdigitated fashion is the preferred construction. Such a construction allows a sheet of liquid or substance to be contacted uniformly thereby ensuring an accurate reading.

The wire traces 62a, 62b are insulated by a substance whose effects on the capacitative property of the capacitor 63 are minimal, yet known. Kapton is such a material. Preferably, the wire traces 62a, 62b are fixed between a laminate 61 of kapton such that the wire traces 62a, 62b are covered above and below. A capacitor 63 made according to the present invention and constructed of copper wire traces 62a, 62b positioned between a laminate 61 of kapton will produce a capacitance of approximately 7 picofarads when surrounded by air.

Figure 6:
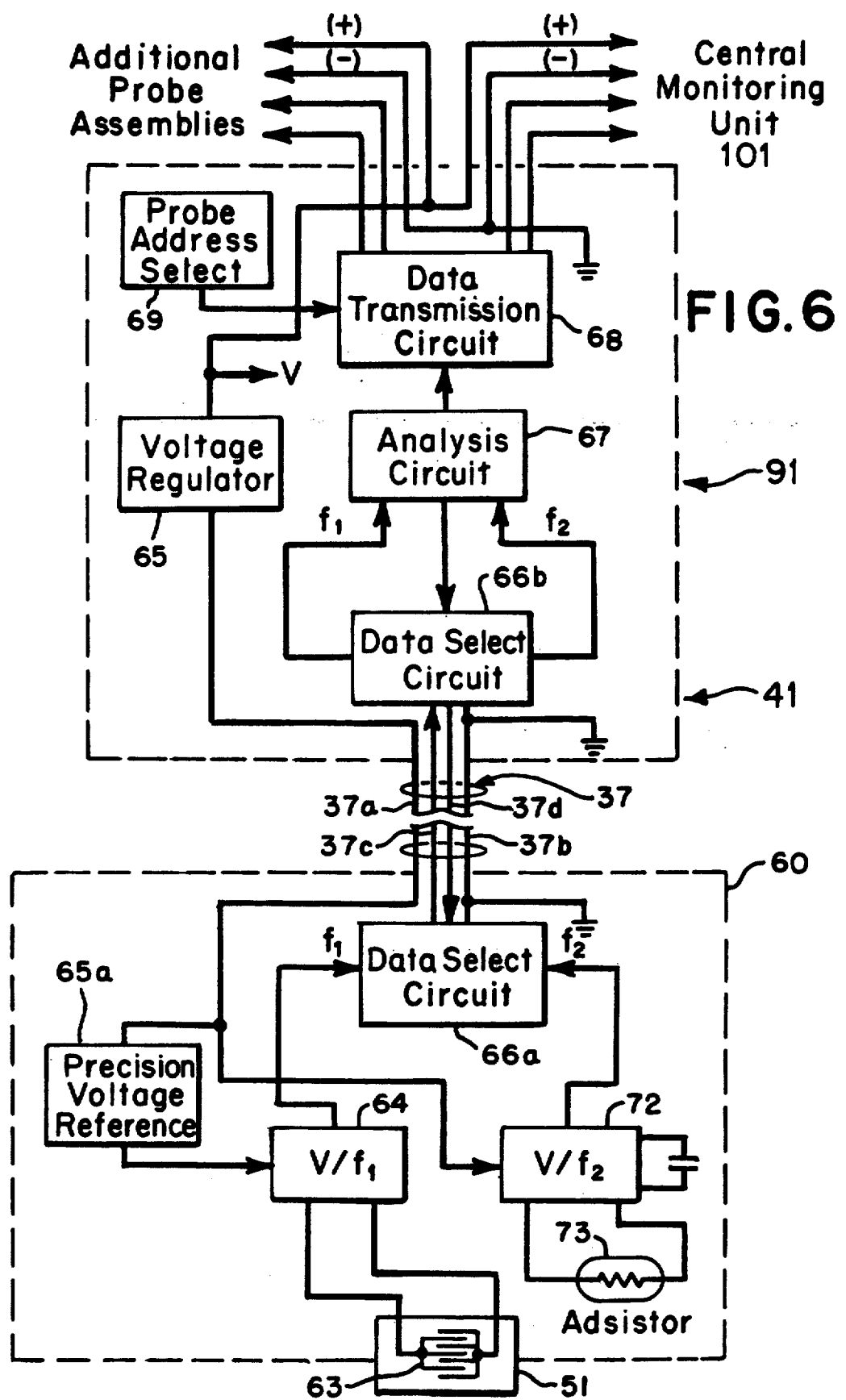
FIG. 6 is a block diagram illustrating the operation of the present invention.
Figure 7:
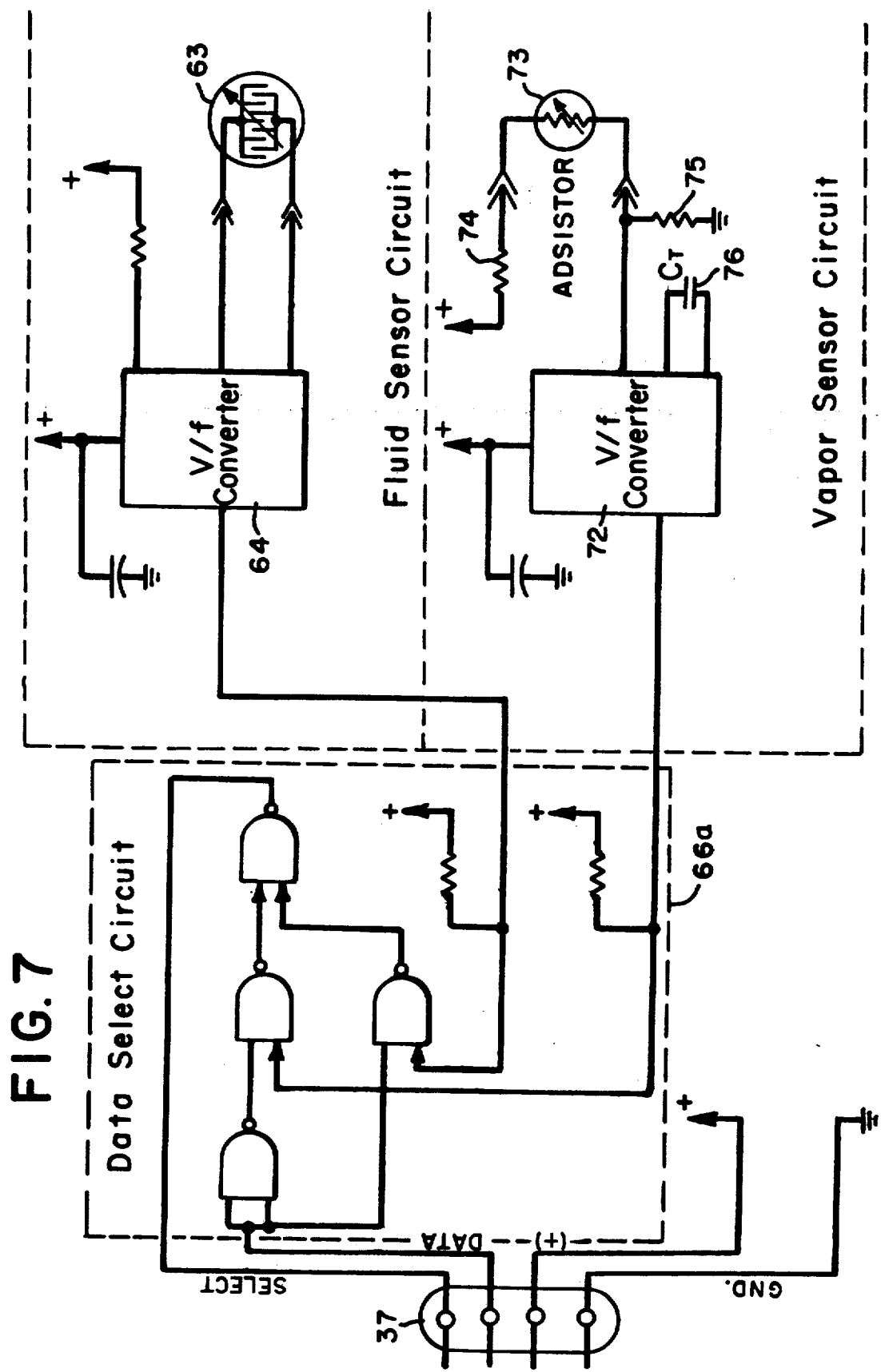
FIG. 7 is a schematic diagram of the sensor circuitry of the detection system.

Referring to FIGS. 6 and 7, the sensor unit 51, which electrically comprises a variable capacitor 63, is connected to a conventional voltage-to-frequency converter 64, such as the type AD654 V-TO-F converter manufactured by Analog Devices. In the operation of this device the applied voltage is held constant, such as by precision voltage reference 65a. Voltage is supplied through conductor 37a by a voltage regulator circuit 65 contained in the cap 91. As a result, the output frequency $f_1$ of the device varies as the capacitance of capacitor 63 changes, which serves as the timing capacitor of the device. As the capacitance of capacitor 63 changes with the non-solid substance contacting the capacitor, the output frequency of the converter changes.

In practice, the capacitance of variable capacitor 63 may be approximately 7 picofarads in air, 16 picofarads when covered by petroleum product, and 57 picofarads when covered by water. The capacitance is translated by the converter to yield an output frequency $f_1$ of, for example, 140 kilohertz in air, 110 kilohertz when covered by a petroleum product, and 40 kilohertz when covered by water. The relationship is inversely proportional. Such wide divergence in frequency values are advantageously easy to distinguish.

The output of converter 64 is applied through data select circuits 66a and 66b in the probe 41 and cap 91, respectively, to a signal analysis circuit 67 in the cap 91, wherein a frequency analysis is accomplished to determine the presence of certain fluids at capacitor 63.

The cap 91 receiver comprises an "intelligent" frequency counter. For example, it may be an Intel 80C31BH microcontroller programmed to track frequency variations. The algorithm used by the microcontroller may establish baseline values for the ambient dry condition. It may recognize and filter out variations of the frequency due to ambient relative humidity and temperature changes. The algorithm recognizes a rapidly changing trend and attempts to determine the cause. In the current implementation, the probe output frequency is analyzed twenty times per second. At this rate, a determination is made if the change in capacitance is due to temperature or humidity fluctuations or by the actual presence of a fluid.

For any given fluid contact with the probe 41 the dielectric constant influences the baseline frequency, producing a "signature frequency" for each type of fluid. Once a fluid signature for a particular monitored fluid is determined, the microcontroller signals an alarm when that fluid is present.

The output of analysis circuit 67, indicating the presence of a monitored fluid, may be conveyed to a central monitoring system. To this end, the cap unit 91 preferably includes a data transmission circuit 68 which forms a packet signal for transmission to a central monitoring unit 101. A unique probe address selected by an address selection circuit 69 is conveyed with the packet signal on a single cable 71 common to all of the probe assemblies of the system.

Figure 9A:
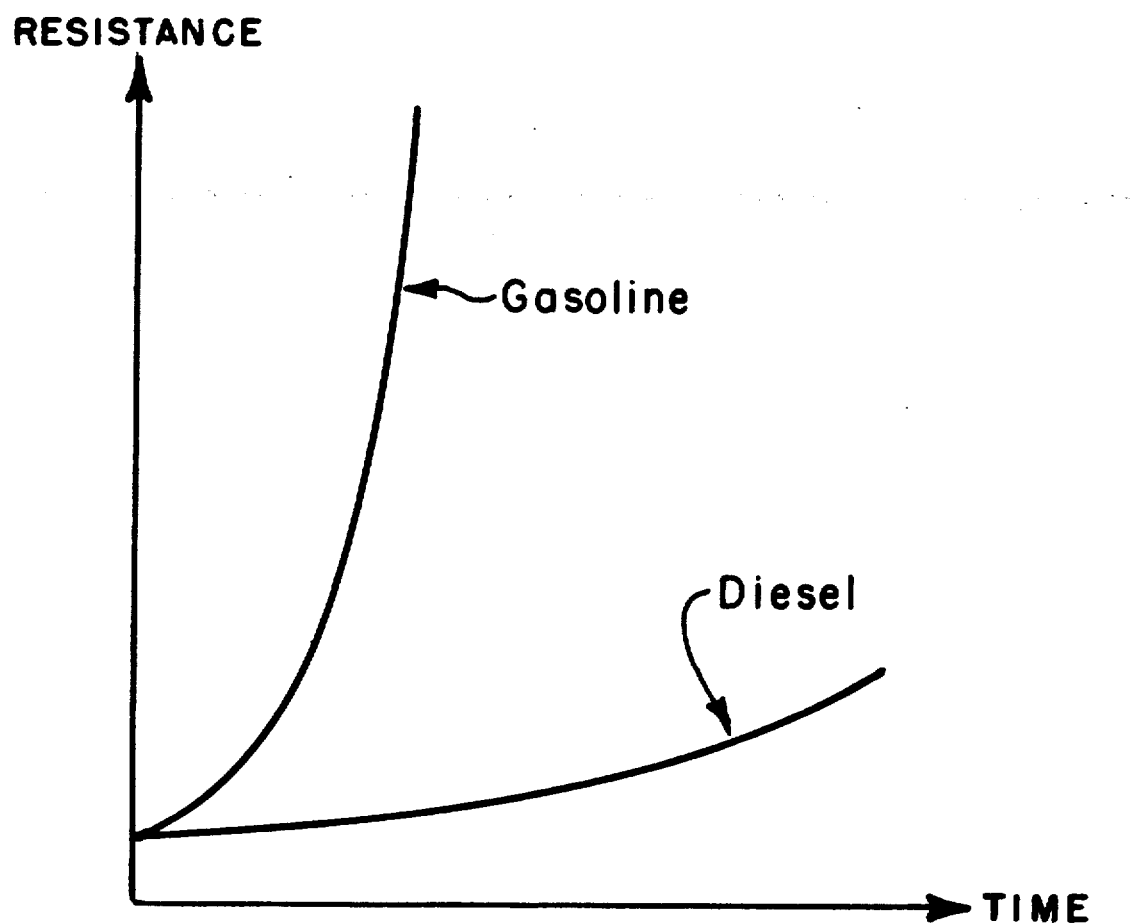
FIG. 9A illustrates the effect that exposure of the present invention to gasoline vapor and diesel oil vapor has on the resistance developed across the adsistor circuitry.

Data select circuits 66a and 66b allow analysis circuit 67 to select between converter 64, which monitors for fluid presence, and a second converter 72, which monitors for the presence of vapor such as gasoline vapor. In particular, converter device 72, which may be identical to converter device 64, operates in conjunction with an adsistor 73 positioned in the probe so as to be subjected to resident vapors. The adsistor, which may be a conventional device such as manufactured by Adsistor Technology, of Seattle, Wash., changes resistance over time with exposure to vapors, as shown in FIG. 9A. Such resistance may vary according to the type of vapor absorbed onto the face 215 of the adsistor. The adsistor is connected in a voltage divider network with resistors 74 and 75, so that the voltage applied to converter 72 varies with exposure of the adsistor to vapor. A fixed timing capacitor 76 is provided, so that those voltage changes result in frequency changes in the output signal generated by the converter. When this signal is selected by data select circuits 66a and 66b, an analysis of the frequency is performed by analysis circuit 67 to determine the status of vapor at the probe. An appropriate output signal is provided to the central monitoring unit 701 through data transmission circuit 68.

In this way, an indication is obtained at the central location of fluid status and vapor status at each probe location in the system. Such an indication may be seen for one or many probes 41 on a display 105 of the central unit 101 at the central location 111, or for any one probe 41 on a display 95 of the cap 91 of the probe 41.

Figure 8:
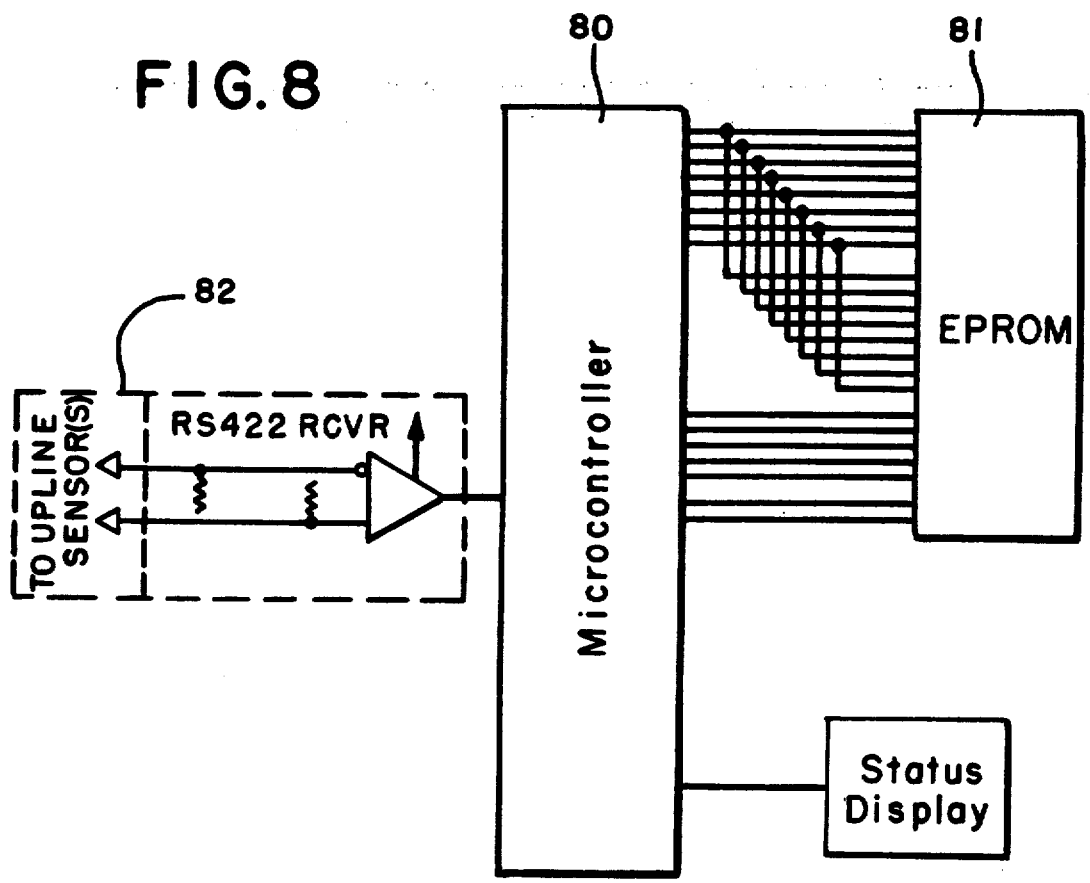
FIG. 8 is a simplified schematic diagram of the display.
Figure 8A:
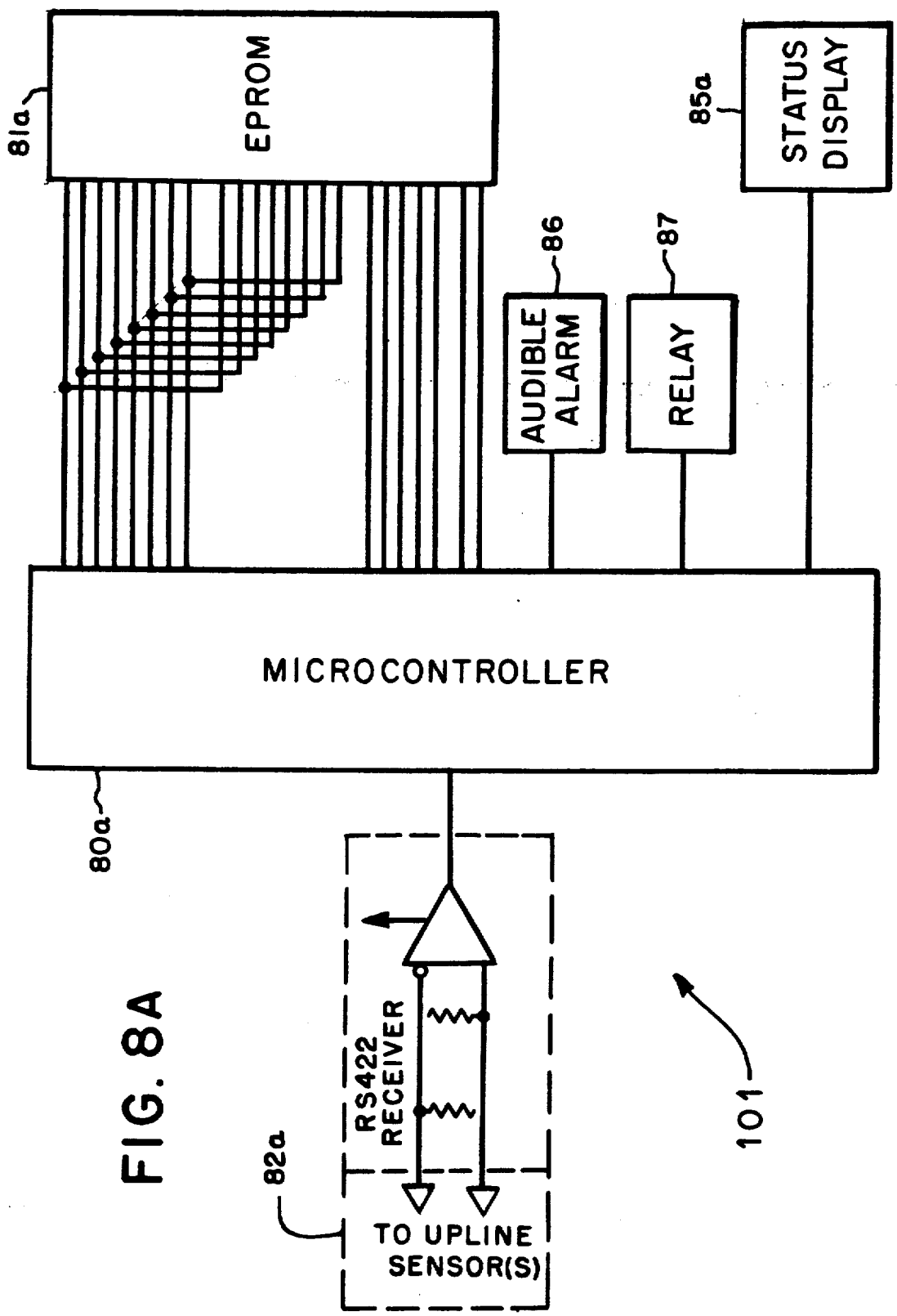
FIG. 8A is a simplified schematic diagram of the display at the central monitoring unit.

Referring to FIG. 8, the functions of the data select circuit 66b, the analysis circuit 67 and the data transmission circuit 68 may preferably be combined in a microprocessor system. In particular, a microcontroller 80, which may, for example, be a type 8031 CMOS device, may be combined with an EPROM 81, which may, for example, be a type 8764 device, to perform necessary signal analysis and control algorithms to provide the aforementioned status indicating output signals.

Output signals in packet form may be received from up-line probe assemblies by a conventional RS422 receiving circuit 82, and conveyed to down-line probe assemblies or the central monitoring station by an RS422 transmitting circuit 83, or the like. Address selection is provided by probe address selection circuit 69, which is seen to include multiple selector switches 84 connected to microcontroller 80. An LED status indicator 85 powered from the microcontroller provides an indication at the local display 95 or remote display 105 of probe status.

In operation, microcontroller 80, operating in conjunction with EPROM 81, periodically samples probe status by periodic application of a control signal to the probe data select line in cable 37. The frequencies of the resulting signals are analyzed by application of appropriate algorithms.

The algorithm functions include the following. Upon power-up, the sensor baseline value is determined. If found within a certain region, the sensor is considered to be not currently exposed to any fluids, and that value—the dry values differ from the baseline value—is made the baseline value. If frequency value, then the sensor is considered to be exposed to some material. An average known value is then used for the baseline value. The algorithm looks for small slow changes in the sensor output, and, if found, adjusts the baseline value for temperature changes. When a rapid change occurs in the sensor output, the effect is considered to be caused by a fluid or substance adjacent to the sensor. The algorithm examines the new value and compares the value with region boundaries, which are calculated from the baseline value. If the value is found to fall within certain signature regions, then a match is found and the fluid is known.

The algorithm output is combined with a probe address signal to generate probe condition packet signals. These are transmitted downline following receipt and retransmission of a similar packet signal from an upline probe, or in the event no packet signal is received, after a predetermined time interval. In this manner, all probes in the system can be connected in a "daisy-chain", communicating to the central monitoring station 111 over a single cable 71 as shown in FIG. 1.

The packet signal is transmitted from each probe assembly and may include a probe address by which the location of the probe assembly may be uniquely identified, a summary status message by which the current status of each sensor is identified, and/or the digitized frequency values from each sensor for historical data trending of the information and/or other analyses performed, for example, at the central console. The incoming packet signals transmitted previously from each cap may be added onto the current packet signal and be retransmitted. Packet signal transmission preferably may occur at least every two seconds.

The probe assembly 41 includes a housing 42 preferably made from a material that is relatively light in weight and does not react, corrode, or oxidize in the presence of humid or wet conditions. Among the materials from which housing 42 may be constructed is polyvinyl chloride (PVC).

Housing 42 is preferably sized and shaped to contain and to facilitate the deployment of the sensor 51, and circuitry 60 arranged therein approximate to an accumulation area 35. For example, one such accumulation area 35 is the floor of a monitoring pipe 30. Monitoring pipes 30 typically are circular in cross section and some two inches in diameter. To facilitate the deployment of the probe assembly 41 onto such an accumulation area, the probe assembly 41 must be sized and shaped so it may be lowered down such a pipe 30. For such deployment, housing 42 is preferably configured in a cylindrical shape as shown in the accompanying Figures, including FIGS. 3A, 3B, and 4. Specifically to construct a probe assembly 41 for deployment within a monitoring pipe 30, housing 42 may be made from 1¼" slip-to-slip Sch. 40 PVC coupling. A probe assembly 41 having a housing 42 constructed in a cylindrical shape and from this material can travel freely within a standard two inch monitoring pipe 30.

Further, in order to facilitate the maximum exposure of the flat variable capacitor 63 to any fluid or substance accumulated on the floor 30 of a monitoring pipe, the capacitor 63 is positioned such that a sensing face 55 of the capacitor is parallel to, yet recessed inward from the face 43 of housing 42. Accordingly, the sensing face 55 does not rest directly on the accumulation area 35. Contacting the accumulation area 35 directly with the sensing face 55 is particularly disadvantageous as anomalous signals would result due, in part, to the generally humid or moist conditions present in such areas 35.

To facilitate the lowering of a probe assembly 41 onto such an accumulation area 35 the cable 37 preferably extends from an end 44 of housing 42 opposite the face 43.

To facilitate the deployment of the probe assembly 41 in other accumulation areas 35, such as the inner basal area 30a of the interstitial space between the double walls of an underground storage tank, or the floor 32a of a containment chamber 32 of an underground storage tank system, the probe assembly 41 may be accordingly sized and shaped. Underground storage tanks, particularly those made of a material such as fiberglass, typically do not have a monitoring pipe positioned generally outside the outer wall but one that extends in and around at least half of the circumference of the interstitial space. For such an application, a flatter design for housing 42 is preferably utilized such as illustrated in FIGS. 5A, 5B, and 5C. In such an embodiment, the capacitor 63 may be positioned recessed from the face 43 of one portion of the housing 42. A flat design as illustrated in FIGS. 5A, 5B, and 5C is suitable for deployment also onto a accumulation area 35 such as the floor 32a of a containment chamber 32.

Figure 9C:
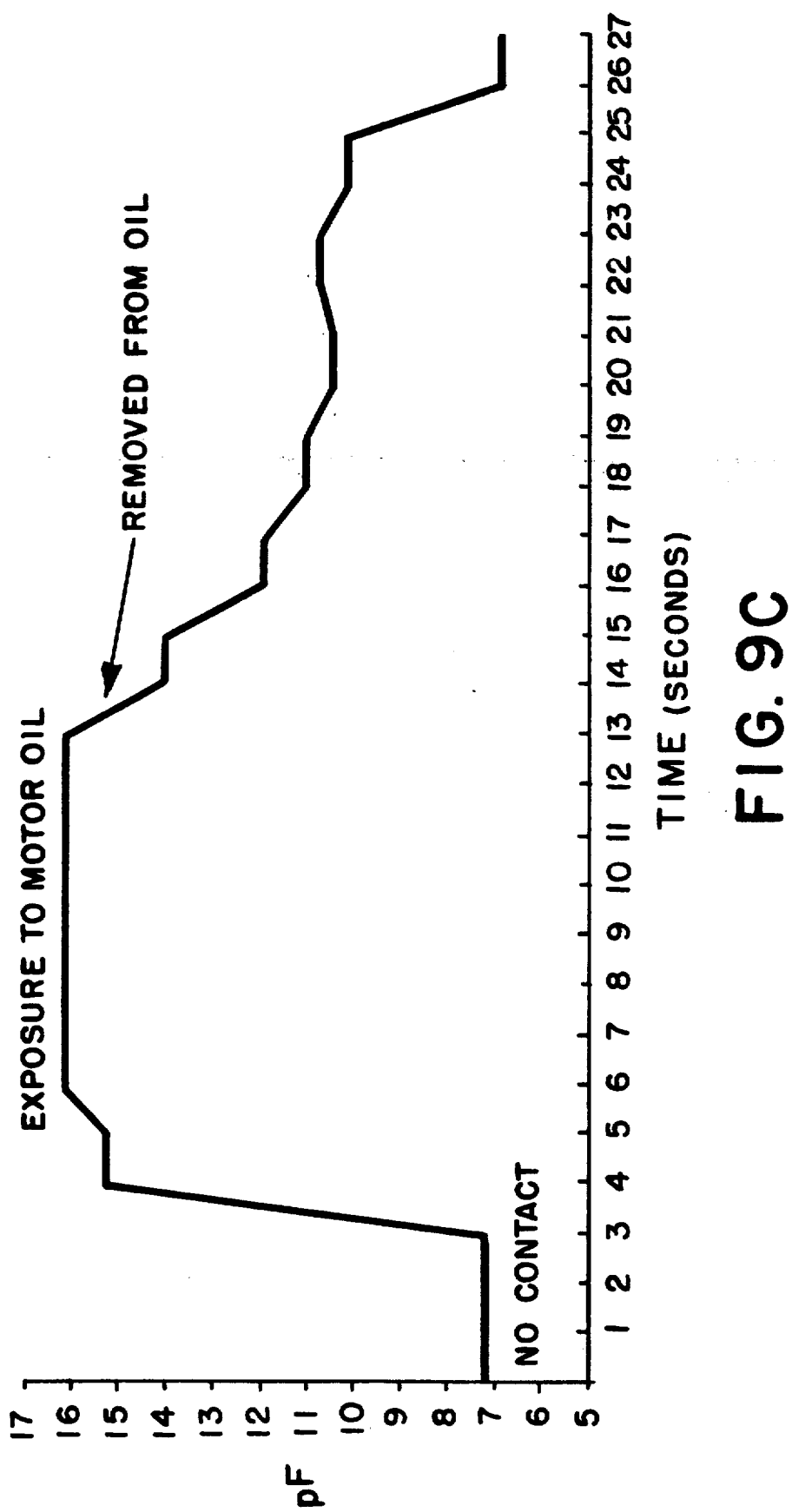
FIG. 9C illustrates the effect that exposure of the present invention to air and to motor oil fluid has on capacitance developed across the capacitor circuitry.
Figure 9D:
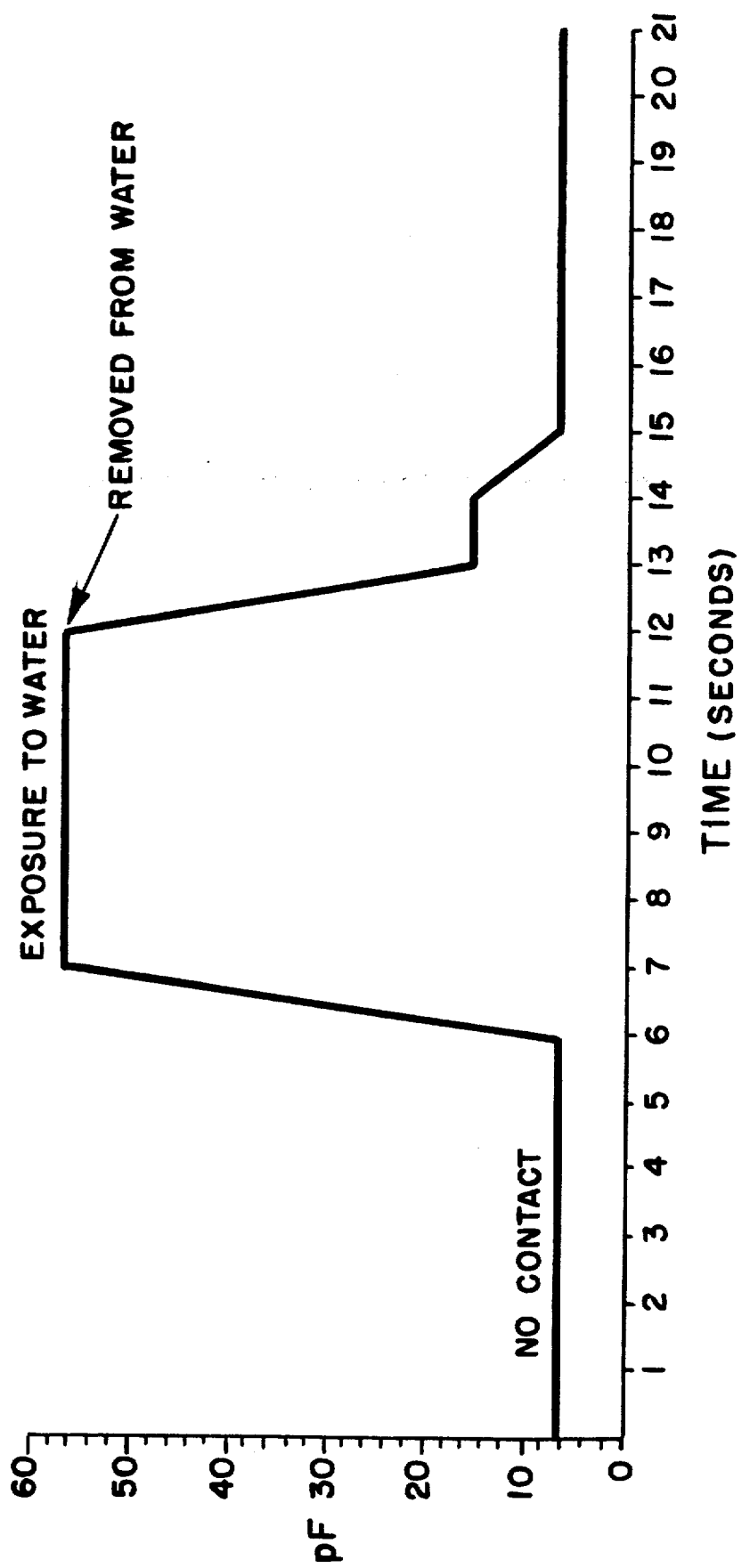
FIG. 9D illustrates the effect that exposure of the sensor according to the present invention to air and to tap water fluid across the capacitor circuitry.

The system 31 is capable of distinguishing between air, water, and a variety of fluids, such as those commonly stored in underground storage tanks. FIGS. 9B, 9C, and 9D illustrate the performance of the system 31 as exposed to three substances. As shown in FIG. 9D, a capacitor 63 according to the present invention and in the presence of air will provide a capacitance value of approximately 7 picofarads. However, when the capacitor 63 encounters tap water, the capacitance developed across the capacitor 63 quickly climbs to approximately 57 picofarads. When the capacitor 63 no longer encounters the water, the capacitance developed across the capacitor 63 quickly drops to its original value.

As shown in FIG. 9C, the capacitor 63 upon encountering motor oil develops a capacitance value of approximately 16 picofarads across the capacitor 63. Upon removal of, and due to the viscosity of the motor oil, the capacitance drops slowly. However, as shown, in some thirteen seconds, the output signal from the capacitor 63 indicates the presence of air only. The time the capacitor 63 will take to recover will depend upon the viscosity of the material to be monitored.

As shown in FIG. 9B, the capacitor 63 will develop a completely different capacitance when exposed to gasoline. Upon the capacitor 63 encountering gasoline, a capacitance of approximately 15.75 picofarads will develop across the capacitor 63. Upon removal of the gasoline, the capacitance drops quickly to its original "in-air" state.

The digitized signal transmitted from the probe assembly 41 is displayable in a variety of formats. For example, in FIG. 10A, the display 95 of a cap 91 is shown that may be locally positioned near to the deployment location of the probe assembly—such as over the monitoring pipe 30 when a probe assembly 41 is positioned therein. The display 95 includes an indicator 85 which identifies whether the probe assembly 41 is encountering air, water, or hydrocarbons. Similarly, the output signal may be displayed remotely, such as by a display 105 on a console 101. A display 105 in the form included in a console 101 can output signals from one or many accumulation areas. The display 105 may include an indicator 85a which identifies whether one or more probe assemblies 41 are encountering air, water, or hydrocarbons.

The packet signal of all probes in the "daisy-chain" are received by the receiver 82a and sent onto the microcontroller 80a. The microcontroller 80a examines all incoming packet signals and activates a relay 87 and an audible alarm circuit 86 if the status contains an indication of a fluid found adjacent to the sensor. The current status is displayed, along with an indication of probe address, on a display indicator 85a.

It will be understood that the embodiments of the present invention which have been described are illustrative of some of the applications of the principles of the present invention. Numerous modifications may be made by those skilled in the art without departing from the true spirit and scope of the invention.

I claim:

1. A fluid detection system for identifying the presence or absence and the identity of fluids within confined areas within an underground storage tank system, said confined areas including accumulation areas on which fluids unintentionally or accidentally entering the confined area can generally accumulate, said fluid detection system comprising:
   a probe assembly sized and shaped for deployment within said confined areas and adjacent to one of said accumulation areas, said probe assembly including a sensor for detecting the presence or absence and identity of said fluids collecting on said one of said accumulation areas;
   said sensor including capacitor means that develops a capacitance characteristic of air or said fluids that contact said capacitor means;
   said probe assembly including a converter responsive to the capacitance of said capacitor means for generating a variable frequency output signal;
   an analyzer unit including circuitry by which said variable frequency signal is edited to provide selected frequencies as an edited output signal; and
   a transmitter for digitalizing and transmitting said edited output signal to a display, said display for indicating the presence or absence and the identity of said fluids within said one of said confined areas or a multiple of said confined areas, whereby said fluids unintentionally or accidentally entering said tank system are identified and displayed.

2. The system according to claim 1, wherein said capacitor means include wire traces arranged flat and forming a sensing face across which said air or said fluids are contacted.

3. The system according to claim 1, further including a housing in which said sensor is contained, said housing having a face on which said probe assembly can rest on said one of said accumulation areas and inward from which said capacitor means is recessed such that said capacitor means is positionable approximate to but separate from said one of said accumulation areas.

4. The system according to claim 1, wherein said capacitor means operate using a low-voltage, low-current source, whereby said probe assembly is made intrinsically safe.

5. The system according to claim 3, wherein said housing is cylindrically shaped and includes an outer wall whose diameter is less than the inner diameter of a monitoring pipe within said tank system, whereby said sensor is of a suitable diameter for deployment within said monitoring pipe.

6. The system according to claim 2, further including a housing surrounding said sensor such that said sensor can be deployed within said confined areas.

7. The system according to claim 6, wherein said housing includes a face on which said housing can rest on one of said accumulation areas and inward from which said sensing face is recessed, whereby said sensing face is positionable adjacent to but separate from said one of said accumulation areas.

8. System for detecting the presence of fluids or gases unintentionally or accidentally entering confined areas within a plurality of underground storage tank systems, each of said confined areas including accumulation areas on which said fluids and adjacent to which gases can collect, said apparatus comprising:
   a plurality of probe assemblies sized and shaped for positioning within said confined areas, each of said plurality of probe assemblies including a sensor that responds to contact with said fluids or said gases by developing a capacitance generally characteristic of said fluids or said gases;
   said each of said plurality of probe assemblies including conversion means by which said voltages are received and are converted to frequencies, said frequencies provided as a converted output signal;
   said each of said plurality of probe assemblies further including means by which said converted output signal is filtered to remove noise and frequencies of non-selected fluids, said filtering means providing a filtered output signal;
   a transmitter by which said filtered output signal from said converting means is digitalized and transmitted to a display; and
   said display for indicating the presence or absence of said fluids or said gases unintentionally or accidentally entering or developing in or around one or more of said accumulation areas, whereby leakage in said plurality of said underground storage tank system is detachable.

9. The detectable system according to claim 8, wherein said each of said probe assemblies includes a housing in which said sensor is contained and by which said sensor is positionable adjacent to one of said accumulation areas.

10. The detection system according to claim 9, wherein said housing includes a face inward from which said sensor is recessed such that said sensor can rest adjacent to but separated from said one of said accumulation areas.

11. The detection system according to claim 8, wherein said sensor includes insulated wire traces forming thereby a sensing face by which said air or said fluids can be contacted.

12. The detection system according to claim 11, wherein said each of said probe assemblies includes a housing in which said sensor is contained and by which said sensor can be positioned adjacent to said one of said accumulation areas.

13. The detection system according to claim 12, wherein said housing includes a face on which said housing can rest on said one of said accumulation areas.

14. The detection system according to claim 13, wherein said sensing face is recessed inward from said face of said housing, whereby said sensing face is positionable adjacent to but not in direct contact with said one of said accumulation areas.

15. The detection system according to claim 8, wherein said each of said probe assemblies includes connection means by which said each of aid probe assemblies can be positioned into said confined areas.

16. The detection system according to claim 8, wherein each said of capacitors operates using a low-voltage, low-amperage power source, whereby said system is made safer.

17. The detection system according to claim 15, wherein said each of said probe assemblies positioned within said confined areas includes a cap positioned at or approximate to ground level and which indicates the presence or the absence of said fluids or said gases within said confined areas.

18. Method of monitoring an underground storage tank system for presence of fluids o gases unintentionally or accidentally entering confined areas within the system, said system including a storage tank buried at least partially below the surface of surrounding ground, said confined areas including accumulation areas on which the fluids or adjacent to which the gases can accumulate or develop, said method comprising the steps of:

positioning one or more probe assemblies into each of one or more of the confined areas such that a sensor of each of said probe assemblies is approximate to, but separate from the accumulation areas;

each of said probes defining a flat variable capacitor, the capacitance of said capacitor directly varying according to the presence or absence and type of the fluids or the gases that contact said capacitor;

developing a signal having a frequency dependent on the capacity of said capacitor;

transmitting said frequency signal as an output signal;

processing said signal to remove non-selected frequencies caused by noise or by ambient conditions, said processing step producing an edited signal;

digitizing said edited signal;

transmitting said digitized edited signal to a display; and indicating on said display the presence or absence of the fluids or the gases that have accidentally or unintentionally contacted said capacitor.

19. The method of claim 18, further including the step of initiating an audible alarm remote from said sensor when the fluids or the gases are detected by said probe assembly.

20. The method of claim 18, wherein said displaying step includes the step of differentially identifying on said display the fluids or the gases that contact said capacitor.

21. A system for reliably monitoring for fluids or gases accidentally or unintentionally collecting on or adjacent to accumulation areas within an underground storage tank system, said system comprising:

a plurality of probe assemblies, each of said probe assemblies sized and shaped to be deployed within said tank system and on said accumulation areas;

said each of said probe assemblies including a sensor that develops a capacitance characteristic of said fluids or said gases that contact said sensor, said sensor sized and shaped to be positioned adjacent to but separate from said one of said accumulation areas whereby at a minimum a thin layer of said fluids or said gases that collects on or adjacent to said accumulation areas can contact said sensor;

said each of said probe assemblies including a converter for producing an output signal having a capacitance characteristic frequency dependent on said capacitance characteristic;

said each of said probe assemblies including a frequency counter by which frequencies caused by noise or ambient conditions can be edited from said output signal to form an edited signal;

said each of said probe assemblies including means to form a digitized signal; and means by which said digitized signal is transmitted to a remote display on which the presence of said fluids or said gases detected by one or more of said plurality of probe assemblies an be reliably indicated.

22. The system according to claim 21, wherein said sensor is insulated with a substance whose effect on said capacitance developed by said sensor upon contact by said fluids or gases is known, said sensor as insulated providing a sensing face.

23. The apparatus according to claim 21, wherein said sensor includes wire traces arranged flat whereby said thin layer of said fluids or said gases are contact uniformly.

24. The apparatus according to claim 23, wherein said wire traces are insulated by a substance whose effect on the capacitance developed by said sensor upon contact by said fluids or gases is known, said wire traces as insulated forming a sensing face.

25. The apparatus according to claim 22, wherein said probe includes a housing in which said sensor is contained, said housing including a face on which said housing rests on said accumulation area and recessed from which said sensing face is positioned adjacent to but separate from said accumulation area.

26. The apparatus according to claim 24, wherein said probe assembly includes a housing in which said sensor is contained, said housing including a face on which said housing rests on said accumulation area and recessed from which said sensing face is positioned adjacent to but separate from said accumulation area.

27. The apparatus according to claim 26, wherein each of said plurality of said probe assemblies includes a receiving circuit by which digitalized signals from said plurality of probe assemblies can be received by one of said probe assemblies and retransmitted to other of said plurality of probe assemblies or said display.

28. The apparatus according to claim 27, wherein said apparatus operates using a low voltage, low current power source.

29. The apparatus according to claim 21, further including a cap positioned at or approximate to one of said probe assemblies and on which the presence of said fluids or said gases detected by said one of said probe assemblies is indicated.

* * * * *